(12) United States Patent
Chatterjee et al.

(10) Patent No.: US 9,933,372 B2
(45) Date of Patent: Apr. 3, 2018

(54) LIGHTING DOMES WITH REFLECTIVE GRADIENT AND BROAD SPECTRUM LIGHT SOURCE

(71) Applicant: Graftek Imaging Inc., Austin, TX (US)

(72) Inventors: Romik Chatterjee, Austin, TX (US); Robert Martin Eastlund, Austin, TX (US); Christopher Jan Koci, Katy, TX (US); Archer Forrest Finley, Austin, TX (US)

(73) Assignee: Graftek Imaging, Inc., Austin, TX (US)

( * ) Notice: Subject to any disclaimer, the term of this patent is extended or adjusted under 35 U.S.C. 154(b) by 65 days.

(21) Appl. No.: 14/877,913

(22) Filed: Oct. 7, 2015

(65) Prior Publication Data
US 2016/0025651 A1   Jan. 28, 2016

Related U.S. Application Data

(63) Continuation of application No. 13/826,973, filed on Mar. 14, 2013, now Pat. No. 9,157,867.

(51) Int. Cl.
*H01J 3/14* (2006.01)
*G01N 21/95* (2006.01)
*G01N 21/88* (2006.01)
*G01J 1/04* (2006.01)

(52) U.S. Cl.
CPC ..... *G01N 21/9501* (2013.01); *G01N 21/8806* (2013.01); *G01J 2001/0481* (2013.01)

(58) Field of Classification Search
CPC ................................................ G01N 21/8806
See application file for complete search history.

(56) References Cited

U.S. PATENT DOCUMENTS

| | | |
|---|---|---|
| 4,150,898 A | 4/1979 | Suga |
| 5,032,856 A | 7/1991 | McMinn |
| 5,118,181 A | 6/1992 | Yifrach et al. |
| 5,169,229 A | 12/1992 | Hoppert et al. |
| 6,341,878 B1 | 1/2002 | Chiang |
| 6,611,282 B1 | 8/2003 | Trubko et al. |
| 2006/0180775 A1 | 8/2006 | Paradis |
| 2010/0208980 A1 | 8/2010 | Urban et al. |

OTHER PUBLICATIONS

A.H. Gallas, C.A. Hilbert and A.B. Hitterdal, "Pinhole Optics and Simulators", Jouranl of the SMPTE, vol. 74, Apr. 1965, pp. 321-323.

*Primary Examiner* — Thanh Luu
(74) *Attorney, Agent, or Firm* — John Bruckner PC

(57) ABSTRACT

A lighting dome that can be used to inspect semiconductor wafers can include a small aperture, backlighting, a reflectance gradient and/or a broad spectrum light source.

2 Claims, 3 Drawing Sheets

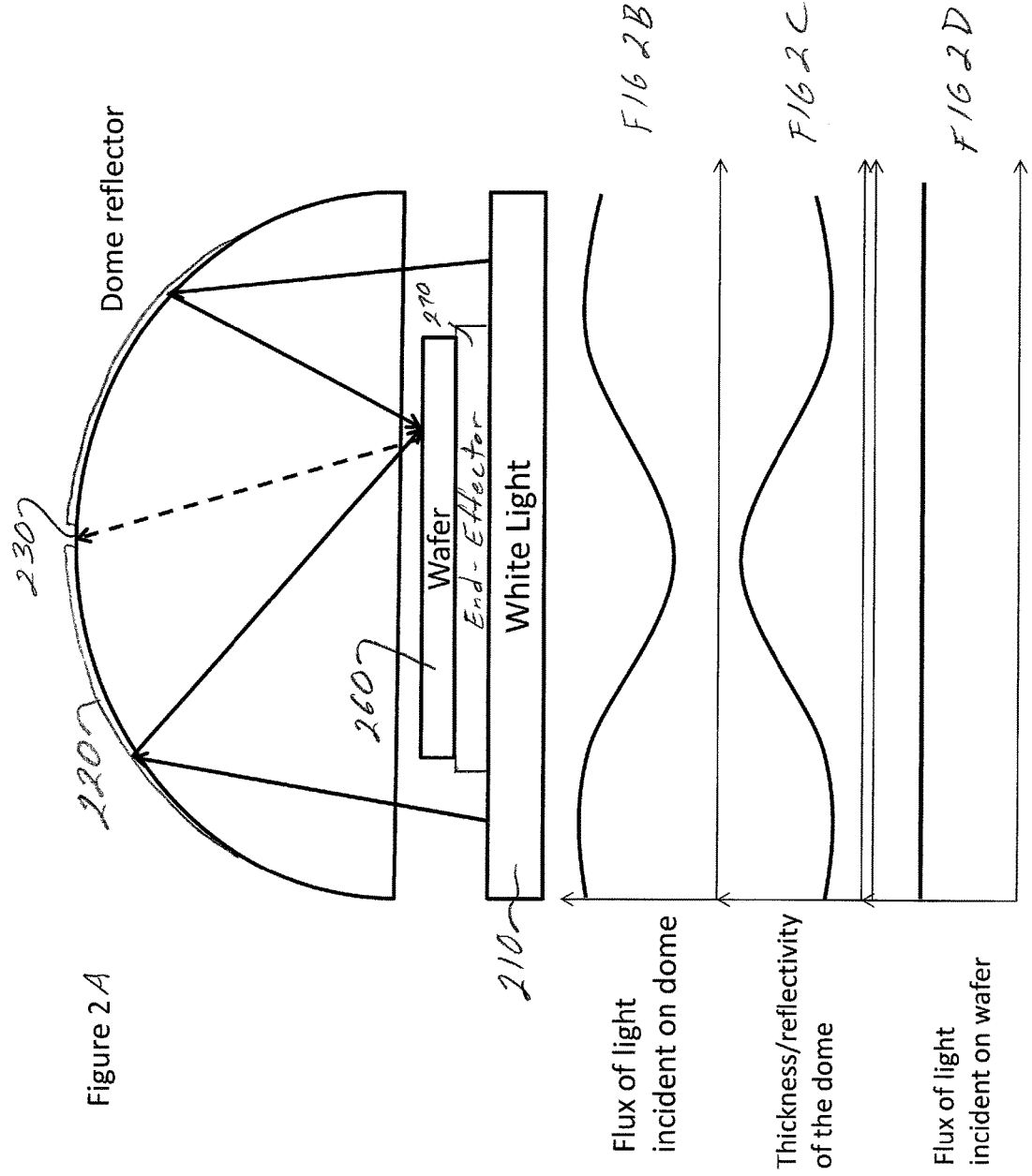

LIGHTING DOMES WITH REFLECTIVE GRADIENT AND BROAD SPECTRUM LIGHT SOURCE

CROSS-REFERENCE TO RELATED APPLICATION

Referring to the application data sheet filed herewith, this application is a continuation of, and claims a benefit of priority under 35 U.S.C. 120 from copending utility patent application U.S. Ser. No. 13/826,973, filed Mar. 14, 2013 the entire contents of which are hereby expressly incorporated herein by reference for all purposes.

BACKGROUND

Prior art lighting domes, are known to those skilled in the art of photography. There are commercial domes for viewing semiconductor wafers that have a large hole in them for the lens to view through. For instance, a conventional dome reflector is typically a hollow hemispherical shell with a reflectively coated interior. Lights located along the interior rim of the shell reflect off the interior to illuminate an object to be viewed. For shiny spherical and convex objects, dome illuminations provide a somewhat diffuse and homogeneous light with less reflection.

Conventional optical systems use a lens with a front element whose size determines the aperture on the dome required to view the wafer. As this aperture size is increased the reflection of the lens in the image of the wafer makes a significant portion of the image unusable. To overcome this and other issues, U.S. Pat. No. 5,684,530 describes a second optical arrangement over the aperture in the dome to allow the illumination of the central spot with a second light source.

However, the disadvantages of this second optical arrangement include the following difficulties. The lighting in the central part through which the camera views the object is not truly multi-directional. The lighting for the central part is from a different light source so the colors and the intensities must be matched to that of the source for the dome making it difficult to use in practice. The height of the light source is increased. The beam-splitter through which the camera views the object can introduce changes to the light passing through it and obstruct the view of the object. What is needed is lighting dome technology that addresses the above-discussed issues in a cost-effective manner.

Meanwhile, the challenges of visual inspection or macro-inspection of semiconductor wafers an applet, a servlet, a source code, an object code, a shared library/dynamic load library and/or other sequence of instructions designed for execution on a computer or computer system).

The term substantially is intended to mean largely but not necessarily wholly that which is specified. The term approximately is intended to mean at least close to a given value (e.g., within 10% of). The term generally is intended to mean at least approaching a given state. The term coupled is intended to mean connected, although not necessarily directly, and not necessarily mechanically. The term proximate, as used herein, is intended to mean close, near adjacent and/or coincident; and includes spatial situations where specified functions and/or results (if any) can be carried out and/or achieved. The term distal, as used herein, is intended to mean far, away, spaced apart from and/or non-coincident; and includes spatial situation where specified functions and/or results (if any) can be carried out and/or achieved. The term deploying is intended to mean designing, building, shipping, installing and/or operating.

The terms first or one, and the phrases at least a first or at least one, are intended to mean the singular or the plural unless it is clear from the intrinsic text of this document that it is meant otherwise. The terms second or another, and the phrases at least a second or at least another, are intended to mean the singular or the plural unless it is clear from the intrinsic text of this document that it is meant otherwise. Unless expressly stated to the contrary in the intrinsic text of this document, the term or is intended to mean an inclusive or and not an exclusive or. Specifically, a condition A or B is satisfied by any one of the following: A is true (or present) and B is false (or not present), A is false (or not present) and B is true (or present), and both A and B are true (or present). The terms a and/or an are employed for grammatical style and merely for convenience.

The term plurality is intended to mean two or more than two. The term any is intended to mean all applicable members of a set or at least a subset of all applicable members of the set. The term means, when followed by the term "for" is intended to mean hardware, firmware and/or software for achieving a result. The term step, when followed by the term "for" is intended to mean a (sub)method, (sub)process and/or (sub)routine for achieving the recited result. Unless otherwise defined, all technical and scientific terms used herein have the same meaning as commonly understood by one of ordinary skill in the art to which this present disclosure belongs. In case of conflict, the present specification, including definitions, will control. include the following issues. The produce can change from one batch to another, thereby changing the expectation of what a good wafer looks like. The product is highly reflective so it is difficult to illuminate without glares. A defect can be hard to define, especially when the failure mechanism is not known. These challenges make manual inspection of the wafers the industry default macro-inspection. But a disadvantage of this approach has been relatively high cost. What is needed is a wafer inspection solution that obviates the above-discussed issues in a cost-effective manner.

SUMMARY

There is a need for the following embodiments of the present disclosure. Of course, the present disclosure is not limited to these embodiments.

According to an embodiment of the present disclosure a method, comprises illuminating a reflective dome with light from a light source; Illuminating an object substantially homogeneously with light reflected by the reflective dome; and sensing light from the object through a small aperture in the reflective dome. According to an embodiment of the present disclosure, an apparatus, comprises: a reflective dome defining a small aperture; and a light source coupled to the reflective dome.

According to an embodiment of the present disclosure a method, comprises illuminating a reflective dome with light from a light source; Illuminating an object substantially homogeneously with light reflected by the reflective dome; and sensing light from the object through an aperture in the reflective dome, wherein the object is located between the broad spectrum light source and the reflective dome. According to an embodiment of the present disclosure an apparatus comprises: a reflective dome defining an aperture; a light source coupled to the reflective dome; and an object holder located between the broad spectrum light source and the reflective dome.

According to an embodiment of the present disclosure a method comprises illuminating a reflective dome having a reflectance gradient with light from a light source; Illuminating an object substantially homogeneously with light reflected by the reflectance gradient of the reflective dome; and sensing light from the object through an aperture in the reflective dome. According to an embodiment of the present disclosure an apparatus, comprises: a reflective dome having a reflective gradient and defining an aperture; and a light source coupled to the reflective dome.

According to an embodiment of the present disclosure a method comprises illuminating a reflective dome with light from a broad spectrum light source; Illuminating an object substantially homogeneously with light reflected by the reflective dome; and sensing light from the object through an aperture in the reflective dome. According to an embodiment of the present disclosure an apparatus, comprises a reflective dome defining an aperture; and a broad spectrum light source coupled to the reflective dome.

According to an embodiment of the present disclosure, a method, comprises illuminating a reflective dome having a reflectance gradient with light from a broad spectrum light source; Illuminating an object substantially homogeneously with light reflected by the reflectance gradient of the reflective dome; and sensing light from the object through a small aperture in the reflective dome, wherein the object is located between the broad spectrum light source and the reflective dome. According to an embodiment of the present disclosure, an apparatus, comprises: a reflective dome having a reflective gradient and defining a small aperture; a broad spectrum light source coupled to the reflective dome; and an object holder located between the broad spectrum light source and the reflective dome.

These, and other, embodiments of the present disclosure will be better appreciated and understood when considered in conjunction with the following description and the accompanying drawings. It should be understood, however, that the following description, while indicating various embodiments of the present disclosure and numerous specific details thereof, is given for the purpose of illustration and does not imply limitation. Many substitutions, modifications, additions and/or rearrangements may be made within the scope of embodiments of the present disclosure, and embodiments of the present disclosure include all such substitutions, modifications, additions and/or rearrangements.

BRIEF DESCRIPTION OF THE DRAWINGS

The drawings accompanying and forming part of this specification are included to depict certain embodiments of the present disclosure. A clearer concept of the embodiments described in this application will be readily apparent by referring to the exemplary, and therefore nonlimiting, embodiments illustrated in the drawings (wherein identical reference numerals (if they occur in more than one view) designate the same elements). The described embodiments may be better understood by reference to one or more of these drawings in combination with the following description presented herein. It should be noted that the features illustrated in the drawings are not necessarily drawn to scale.

FIG. 2A is a schematic side view of a lighting dome that includes a dome reflector having a gradient reflector interior surface and a back light source.

FIG. 2B is an illustration of flux of light incident on the gradient reflector interior surface as a function of position relative to the base plane defined by the edge of the dome reflector.

FIG. 2C is an illustration of thickness/reflectively of the dome as a function of position relative to the base plane defined by the edge of the dome reflector.

FIG. 2D is an illustration of flux of light incident on the wafer (or a plane defined by the wafer) as a function of position relative to the base plane defined by the edge of the dome reflector.

DETAILED DESCRIPTION

Figure 1:
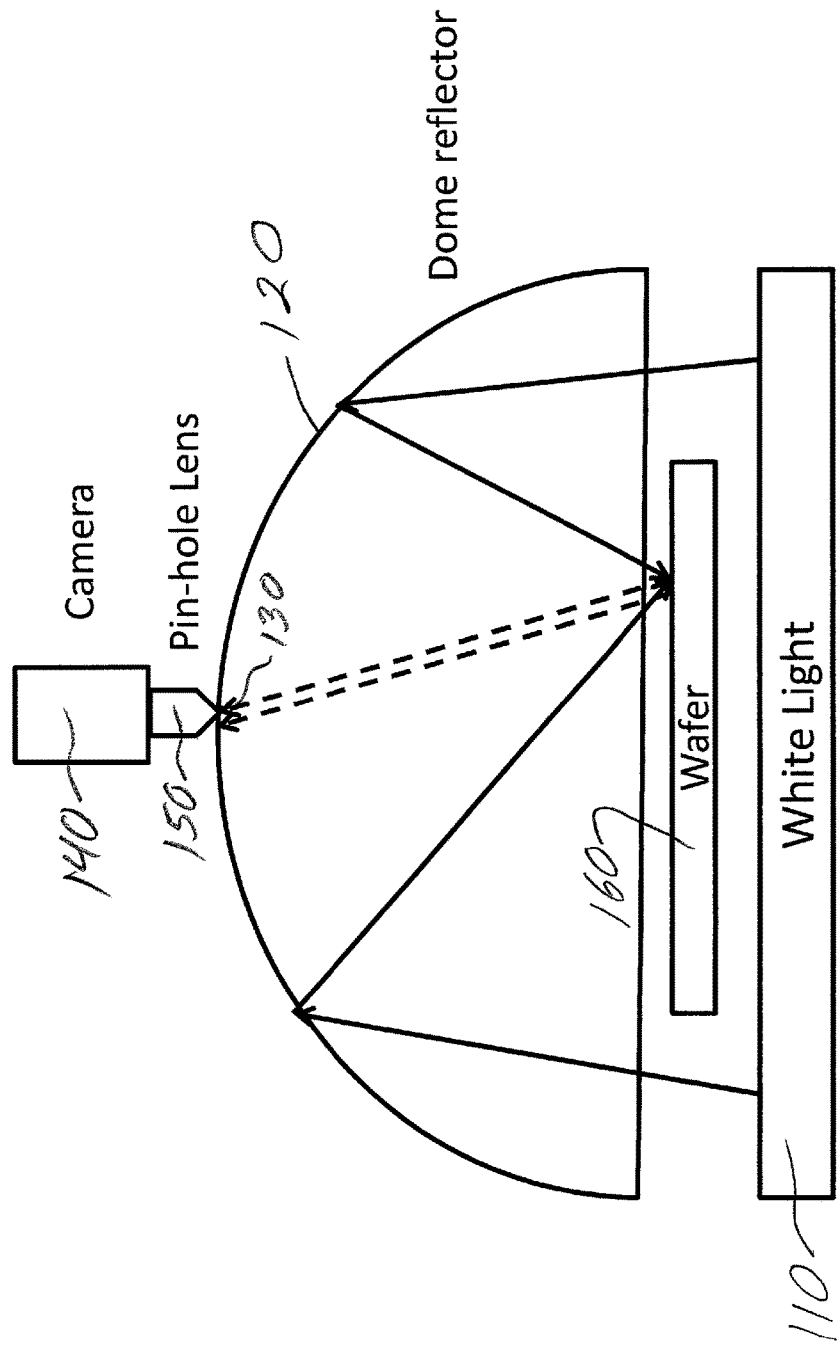
FIG. 1 is a schematic side view of a lighting dome that includes a dome reflector and a back light source.

Embodiments presented in the present disclosure and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the embodiments of the present disclosure in detail. It should be understood, however, that the detailed description and the specific examples are given by way of illustration only and not by way of limitation. Various substitutions, modifications, additions and/or rearrangements within the scope of the underlying inventive concept will become apparent to those skilled in the art from this disclosure.

The below-referenced U.S. Patent(s) and/or U.S. Patent Application(s) disclose embodiments that are useful for the purposes for which they are intended. The entire contents of U.S. Pat. No. 5,684,530 are hereby expressly incorporated by reference herein for all purposes. The entire contents of U.S. Ser. No. 12/704,383 filed Feb. 11, 2010 (U.S. Pat. App. Pub. 2010/0208980, published Aug. 19, 2010) are hereby expressly incorporated by reference herein for all purposes.

Overview

In general, the context of embodiments of the present disclosure can include inspection of semiconductor fabrication wafers. Embodiment of the present disclosure can include a machine vision system. The machine vision system can include a lighting dome. The lighting dome can include a reflective dome (dome reflector). The reflective dome can have a substantially circular edge defining a base plane. The reflective dome can be placed above (over) a semiconductor wafer (or other object of interest to be viewed). The lighting dome can include one or more openings to view the semiconductor wafer. The lighting dome can include one or more light source(s) that are incident upon the reflective dome. The reflected light from the reflective dome can then in-turn illuminate the semiconductor wafer or other object of interest.

More specially, the context of embodiments of the present disclosure can include detection of defects in the manufacturing of semiconductor wafers. This defect detection can be performed one or more times during processing of the wafer itself and/or one or more times during processing of the circuits that are fabricated on the wafer. This defect detection can be performed after processing of the wafer itself is complete and/or after processing of the circuits is complete; before dicing the wafer into individual chips.

For instance, the context of embodiments of the disclosure can include detection of residue on the surface of semiconductor wafers. This residue detection can be performed one or more times during processing of the wafer itself and/or one or more times during processing of the circuits that are fabricated on the wafer. This residue detection can be performed after processing of the wafer itself is complete and/or after processing of the circuits is complete; before dicing the wafer into individual chips.

Small Aperture Reflective Dome

The reflective dome can include an opening at or near the top of the dome; and a camera lens located proximate the opening. The opening can include a small aperture through which the wafer is viewed with a pinhole lens. The small aperture has the advantage of leaving more of the dome's reflective surface intact while still allowing the use of the pinhole lens. The use of the pinhole lens has the advantage of reducing the amount of lens reflection on the surface of the wafer while still allowing the use of the camera. The camera captures an image of the wafer and transfers it to a connected computer where a software algorithm is used to detect variations in the pattern of the wafer. The small aperture can be as small as less than approximately 1 degree (60 minute of arc), preferably less than approximately 6 minutes of arc. In preferred embodiments, the opening is circular and located substantially coaxial with a normal to the base plane, that normal being substantially coaxial with a center of the circular edge.

For example, the aperture in the dome can be minimized to a diameter of approximately 3 mm from a diameter of approximately 25 mm resulting in the following advantages. Approximately 98.56% of the previously unusable area is recovered. The area around the center of the dome has the same multi-directional illumination as the rest of the dome because it is not affected by the missing light from the area of the aperture. For an industry standard 200 mm wafer, 99.975% of the wafer can be inspected if the reflection of the aperture is limited to a 3 mm region. For an industry standard 300 mm wafer, 99.99% of the wafer can be inspected if the region of the aperture is considered unusable in contrast to 92.8% for a commercial dome. The small aperture to view the wafer can be used with the combination of a pinhole lens to view the entirety of the wafer. The size of the dome needed for an even illumination can be minimized. For inspecting a 200 mm wafer the dome needs to be 270 mm in contrast to a commercial dome that is 300 mm. For inspecting a 300 mm wafer the dome needs to be 350 mm in contrast to a commercial dome that is 424 mm.

An exemplary lighting geometry is shown in FIG. 1. A white light source 110 is a flat, diffuse ring light that is directed towards an interior of a dome reflector 120. The dome reflector is a white plastic hemispherical shell with a diffuse interior surface and a small aperture 130 at the top for viewing by a camera 140. In this example, the shell is of uniform thickness, but the shell can be of variable thickness to provide a reflective gradient. In this example, the camera includes a sensor without any optical filters, but the camera can include sensor(s) with optical filters (including color sensors, ultraviolet, Near infrared, etc.). The camera is not limited to a color camera. The camera is coupled to a pinhole lens 150 that is aligned with the small aperture to view a semiconductor wafer 160. In this example, the while light source is located in back of the wafer with regard to the camera.

Back Light Source(s)

Embodiments of the present disclosure can include a reflective dome that is illuminated with lighting from behind (in back of) the wafer or other object of interest. Embodiments of the disclosure can include one or more light source(s) located below (behind) (in back of) the object to be viewed (e.g. the wafer). This means that the wafer or other object of interest, is located between the lighting source(s) and the opening of the dome reflector. In this case, the one or more light source(s) can be termed back light(s). In preferred embodiments, the one or more light source(s) are also located below the base plane of the dome reflector. This means that the base plane of the dome reflector is located between the lighting source(s) and the opening of the dome reflector.

Embodiments of the present disclosure can include the use of one or more (LED) light source(s) to create a backlit image of the wafer. This single LED light source can be in the form of a homogeneous lighting panel upon which the substrate (or other object) is located to be viewed. Embodiments of the present disclosure can include the use of a diffuse dome lit image of the wafer. The diffuse dome lit image can be obtained by coating the interior surface of reflective dome with a film or layer that functions as a physical diffuser.

The light source behind the wafer (back lighting) results in at least the following advantages. A backlit image of the wafer is obtained which allows for determination of the rotation of the wafer based on the location of the notch on the wafer. Substantially even illumination is obtained for the entire wafer for a smaller size of the dome relative to the wafer. The wafer can be placed closer to the dome resulting in a more even illumination over the area of the wafer. Maintenance of the light can be performed without affecting the optical alignment of the camera, lens and the dome. A less expensive flat ring light can be used as the light source. Heat from the light does not affect the dome thus allowing the dome to be made out of less expensive polymer than the metal domes used in commercial lights. The panel provides an angularly homogenous even light source that is then reflected off the dome compared to the discrete LED sources used to illuminate the commercial domes. The panel can be polarized and the light incident on the interior of the reflective dome and, therefore, be polarized.

The wafer or other object of interest that is lit with one or more back light source(s) can be observed with a pinhole lens viewing through a small aperture in the reflective dome. While the small aperture and back light source(s) can be used together in combined embodiments, the small aperture and back light source(s) are independent and separate elements that can be used alone in separate embodiments. This means that embodiments of the present disclosure can include both or just one of the small aperture and/or the back light source(s).

Gradient Reflective Dome

Embodiment of the present disclosure can include a reflective dome that is formed of a (co)polymer or other material that is partially reflective and partially transmissive (translucent). A truly diffuse reflection can be obtained from the polymer dome because the light can (at least partially)

penetrate the first surface of the dome and, in this case, is not reflecting off a coating on a metallic surface. By adjusting the shape, thickness, reflectivity of the inside and outside surface and the diameter of the dome relative to the wafer a radially even illumination can be obtained. See FIG. 2. Note that the dome can be ellipsoidal. While the back light panel may be polarized, the light incident on the surface of the wafer can be random polarization with a diffuse inside surface of the dome acting to randomize the polarization. In this way, the polarization of the light incident on the wafer is truly random. Embodiments of the present disclosure can include a lighting dome including a dome reflector having a reflectivity that changes as a function of an angle to a normal of the base plane, this normal being substantially coaxial with a center of the circular edge of the dome reflector. The term normal in this context means a geometrical line that is perpendicular to the base plane defined by the circular edge of the dome reflector. The phrase normal being substantially coaxial with an axis of the circular edge means the normal passes through a center defined by the circular edge. In preferred embodiments, the reflectivity of the dome reflector increases as the angle to the normal decreases (i.e. increases toward the opening at the top of the dome).

In preferred embodiments, the increase in reflectivity is provided by an increase in thickness of a polymer shell that forms the dome reflector. In this case, the reflectivity decreases as the thickness decreases toward the circular edge. Alternatively, the change in reflectivity can be provided by a reflective coating of variable composition (e.g. a paint with variable metal flake content). In this case, the metal flake content would increase toward the small aperture. Alternatively, the change in reflectivity can be provided by a material (e.g. polymer) whose porosity decreases as the angle to the normal decreases.

Another exemplary lighting geometry is shown in FIG. 2. A white light source 210 is a flat, circular panel that is directed towards an interior of a dome reflector 220. The dome reflector is a white plastic hemispherical shell with a diffuse interior surface and a small aperture 230 at the top for viewing by a camera (not shown in this illustration). In this example, the shell is of variable thickness that defines a gradient that increases toward the small aperture to provide a reflective gradient whereby the reflectivity increases toward the small aperture. In this example, the camera includes a monochromatic sensor, but the camera can include color sensor(s) (2CCD or multispectral). A semiconductor wafer 260 is located on an end-effector 270. In this example, the white light source is also located in back of the wafer.

FIG. 2B shows the flux of light incident on the gradient reflector interior surface as a function of position relative to the base plane defined by the edge of the dome reflector. The lower flux caused by the shadow cast by the wafer, and also the end-effector, can be seen. FIG. 2C shows thickness/reflectivity of the dome as a function of position relative to the base plane defined by the edge of the dome reflector. The increase in reflectivity toward the top of the reflective dome due to the increasing thickness can be seen. FIG. 2D shows flux of light incident on the wafer (or a plane defined by the wafer) as a function of position relative to the base plane defined by the edge of the dome reflector. The flat line shows uniform illumination.

The wafer or other object of interest that is illuminated with light reflected by the gradient reflector dome can be observed with a pinhole lens viewing through a small aperture in the reflective dome. The wafer or other object of interest that is illuminated with light reflected by a the gradient reflector dome can be lit with one or more back light source(s).

While the small aperture, the back light source(s) and the gradient reflector can be embodied together in combined embodiments, the small aperture, the back light source(s) and the gradient reflector are independent and separate elements that can be used alone in separate embodiments or in subcombinations composing two out of three. This means that embodiments of the disclosure can include two, or just one of the small aperture, the back light source(s) and/or the gradient reflector.

Wide Spectrum Light Source(s)

Embodiments of the disclosure can include the use of white (broad spectrum) light reflected by the reflective dome to illuminate a semiconductor wafer or other object of interest. The wafer or other object of interest that is illuminated by one or more broad spectrum (white) light sources can be observed by a unfiltered (monochrome) camera. Thus, embodiments of the present disclosure can include the use of a white (broad spectrum) light source with a broad spectrum integrating camera to integrate the image over a broad spectrum. The use of a broad spectrum light source can improve imaging results and this will be discussed below in more detail.

Figure 3B:
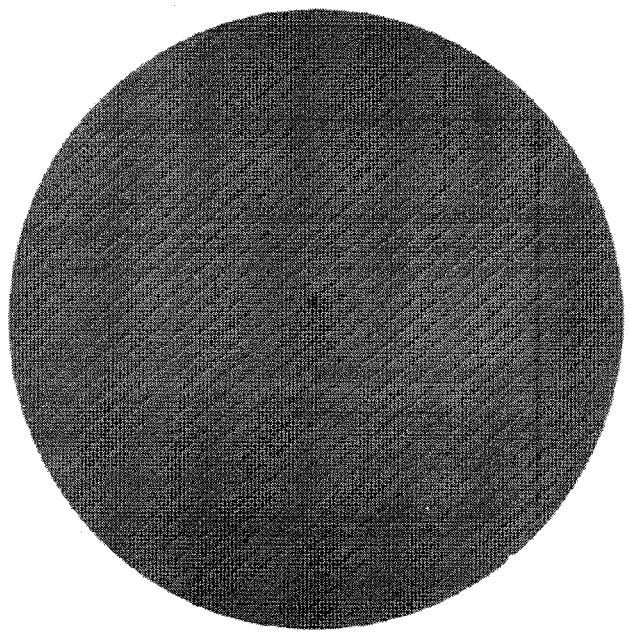
FIG. 3B is a machine vision image of a wafer illuminated by white light (i.e., relatively broad spectrum) that does not show the pattern mentioned above with regard to FIG. 3A.
Figure 3A:
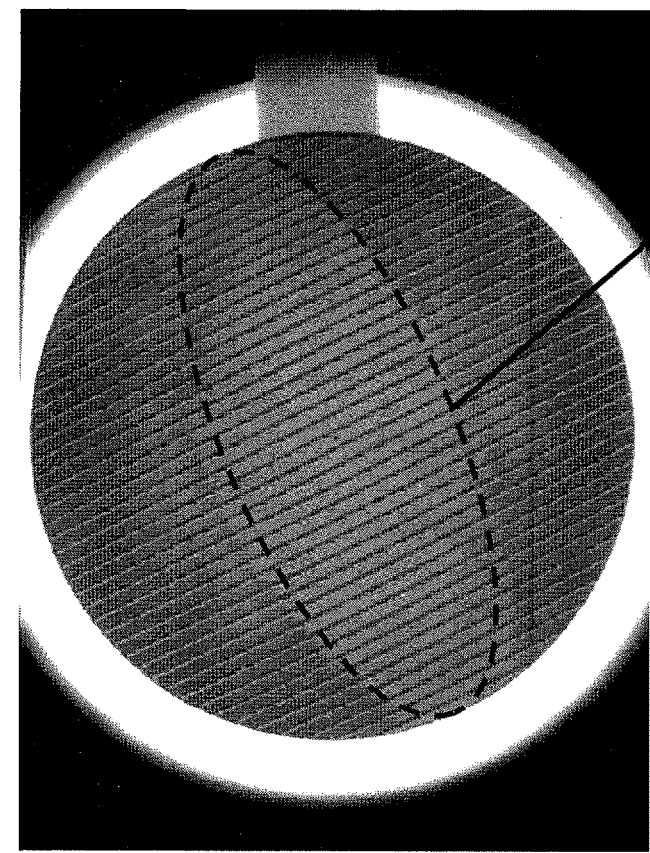
FIG. 3A is a machine vision image of a wafer illuminated by red light (i.e., narrow spectrum) showing an elliptical shaped pattern than can cause a false positive when testing for defects and/or residue.

FIG. 3A shows a machine vision image of a wafer illuminated by red light (i.e., narrow spectrum) showing an elliptical shaped pattern than can cause a false positive when testing for defects and/or residue. FIG. 3B shows a machine vision image of a wafer illuminated by white light (i.e., relatively broad spectrum) that does not show the pattern mentioned above with regard to FIG. 3A. The image of FIG. 3B was obtained using a broad spectrum integrating camera to integrate the image over a broad spectrum.

The wafer or other object of interest that is illuminated by one or more broad spectrum light sources can be observed with a pinhole lens viewing through a small aperture in the reflective dome. The wafer or other object of interest that is illuminated by one or more broad spectrum light sources can be lit with one or more back light source(s). The wafer or other object of interest can be illuminated with light reflected by a gradient reflector dome.

While the small aperture, the back light source(s), gradient reflector and wide spectrum sources(s) can be utilized together in combined embodiments, the small aperture, the back light source(s), the gradient reflector and the wide spectrum source(s) are all independent and separate features that can be embodied alone in separate embodiments or in subcombinations of two or three. This means that embodiments of the disclosure can include three, two, or just one of the small aperture, the back light source(s), the gradient reflector and/or the wide spectrum light source(s).

Residue Detection System

Embodiments of the present disclosure can include a residue detection system (RDS). A residue detection system is a machine vision system used to detect residual metal films on the surface of a semiconductor wafer. The lighting and optics for the vision system can be designed to: view the entire wafer and/or part of the wafer. To this end, the lighting and optics illuminate the wafer evenly across the entire surface to help create an image of the wafer with contrast between the residual metal and the rest of the wafer. The system can utilize one, two or more software algorithms to detect the presence of the residue in the resulting image.

Alternatively, embodiments of the present disclosure can omit the use of software algorithms relying instead on raw data. Embodiments of the present disclosure can even omit the use of a camera or sensor relying instead on observation of the image produced by the lighting source(s), the object(s), the dome, and optionally a pin hole lens.

In those embodiments that utilize one, two or more software algorithms, a first algorithm can use a predetermined threshold to detect pixels that are above a specific (optionally predetermined) intensity. These pixels (areas) are determined (calculated) by the algorithm to be the residual metal.

A second algorithm is designed to detect residue that has the same intensity as the metallic traces on the wafer. The second algorithm: first determines the repeating pattern on the wafer; and second uses the scale of the pattern to look for differences between similar regions. The differences are determined to be regions where there is residual metal. The sensitivity of this second algorithm is dependent on the uniformity of the lighting used to illuminate the wafer. If the illumination is not even, the second algorithm will detect this as a region of difference that will result in a false detection of residual metal.

The conventional method to produce a grayscale image with a monochrome camera is to use a monochromatic light source. When a monochrome camera is used to view the wafer with a monochromatic light, a grayscale image is produced. Regions of the wafer that do not have a metallic residue reflect the light from the dome with a diffuse Lambertian reflectance. Regions of the wafer that have metallic residue reflect the light with a specular reflection component added to the diffuse reflection. When a thick layer of metal is present its specular reflection can be large enough to cause a detectable increase in the intensity of that region. However, when the metal layer is thinner or has a diffuse finish, the intensity of the region is similar to that of the metallic traces running across the wafer.

Referring to FIG. 3A, when the RDS system is built with a red monochromatic source (660 nm) and a monochrome camera the image of some wafers exhibits a pattern that is aligned to the notch of the wafer. This "evil eye" pattern is related to the properties of the surface of the wafer and the dome used to illuminate the wafer. This pattern is not visible in an image of the wafer without the dome. This pattern limits the ability of the algorithm(s) used to detect the residual defects as this pattern causes false failures.

Referring to FIG. 3B, the use of white (broad spectrum) light source(s) with the dome and a broad spectrum integrating (color) camera eliminates the formation of the "evil eye" pattern. This greatly enhances the capability of the RDS system as the algorithm does not have to be desensitized to prevent false failures caused by this pattern. The "evil eye" pattern is also sometimes visible in images of the wafer obtained with a white light and a monochromatic camera. However, via the use of a non-monochromatic camera the intensity of the pattern is greatly reduced in each color plane. Each pixel in a color camera integrates the part of the spectrum of light that is passed by the filter in front of it (red, green or blue). In contrast to a monochromatic light source the broad spectrum of light for each pixel reduces the formation of the pattern. It is important to appreciate that when a white light is used with a broad spectrum integrating camera the pattern is eliminated because of the integration over the entire spectrum at each pixel.

As previously noted, the challenges of visual inspection or macro-inspection of wafers include the following issues. The product (e.g. semiconductor wafer) can change thereby changing the expectation of what a good wafer looks like. The product is typically highly reflective so it is difficult to illuminate without glares. A defect can be hard to define, especially when the failure mechanism is not known.

Embodiments of the present disclosure can overcome the above challenges for at least the following reasons. The software does not need to have been trained with a wafer to be able to inspect it. The software does not have any preset expectations for a wafer. New patterns can be inspected without any training. The illumination is diffuse, uniform and glare free. The defect is identified by a software algorithm that scans the wafer to detect patterns, looks for areas on the wafer that break that pattern.

The sensitivity of the algorithm to detect defects is limited by a) non-uniformities in the patterns on the wafers that may be falsely detected as defects, b) non-uniformities of lighting that may be detected as defects, and c) the appearance of non-uniformities due to the interaction of the thin films on the wafer and the color of the light. The non-uniformities that are detected as defects are abrupt changes in the pixel statistics within the spatial scale of the die. Slower changes across the wafers are not considered to be defects and are not called out as defects by the algorithm.

The first two challenges a) and b) are overcome by tuning the algorithm that is used to detect the defects and designing a uniform lighting system. The last challenge c) is overcome with the use of the white light with a monochrome camera. FIG. 3A shows a region with a dotted line that is brighter than the rest of the wafer when illuminated by a red LED light. Referring to FIG. 3B, the same wafer when illuminated with a white light of the same type does not exhibit the non-uniformity. This allows the software algorithm to detect defects that are of the magnitude of this change, thus allowing the system to be more sensitive.

White Ceramic End-Effector

Embodiments of the present disclosure can include a robotic end-effector to handle the wafer. The robotic end-effector used to present the wafer to the vision inspection system can be made of a white ceramic thus allowing the notch of the wafer to be located when it is placed against the end-effector. When a notch is located at the edge of the end-effector it is still detectable. The robotic end-effector (especially if it is white) can reflect the light incident from the dome and minimizes the perturbation caused by its presence. The white end effector acts as a background to the dark edge of the wafer allowing for a good contrast to detect the location of the notch. The white material of the end effector causes a minimal perturbation in color and intensity to the incident light flux onto the dome and the wafer. The wafer can be placed closer to the dome resulting in the increase of the lighting uniformity across the wafer.

The use of a small aperture in a lighting dome for the inspection of the surface of a semiconductor wafer can be extended to other vision systems. The use of back lighting with a lighting dome for the inspection of the surface of a semiconductor wafer can be extended to other vision systems. The use of a gradient reflective dome for the inspection of the surface of a semiconductor wafer can be extended to other vision systems. The use of white light with a non-monochromatic camera for the inspection of the surface of a semiconductor wafer can be extended to other vision systems. Similarly, the use of a white ceramic end-effector for the inspection of the surface of a semiconductor wafer can be extended to other vision systems. Other systems used for inspection of materials can include polymers, glass, laminates and composites; and all of these systems would benefit from the use of this technique.

An embodiment of the present disclosure can also be included in a kit-of-parts. The kit-of-parts can include some, or all, of the components that an embodiment of the present disclosure includes. The kit-of-parts can be an in-the-field retrofit kit-of-parts to improve existing systems that are capable of incorporating an embodiment of the present disclosure. The kit-of-parts can include software, firmware and/or hardware for carrying out an embodiment of the present disclosure. The kit-of-parts can also contain instructions for practicing an embodiment of the present disclosure. Unless otherwise specified, the components, software, firmware, hardware and/or instructions of the kit-of-parts can be the same as those used in an embodiment of the present disclosure.

The particular manufacturing process used for making the dome reflector should be inexpensive and reproducible. Conveniently, the dome reflector of an embodiment of the present disclosure can be carried out by using any casting, forming or molding method. It is preferred that the process be precise. For the manufacturing operation, it is an advantage to employ a spin casting technique.

However, the particular manufacturing process used for making the dome reflector is not essential to an embodiment of the present disclosure as long as it provides the described functionality. Normally those who make or use an embodiment of the present disclosure will select the manufacturing process based upon tooling and energy requirements, the expected application requirements of the final product, and the demands of the overall manufacturing process.

The particular material used for the dome reflector should be chemically stable. Conveniently, the dome reflector of an embodiment of the present disclosure can be made of any polymer material. It is preferred that the material be a low molecular weight (co)polymer. For the manufacturing operation, it is an advantage to employ a thermoplastic material.

However, the particular material selected for the dome reflector is not essential to an embodiment of the present disclosure, as long as it provides the described function. Normally, those who make or use an embodiment of the present disclosure will select the best commercially available material based upon the economics of cost and availability, the expected application requirements of the final product, and the demands of the overall manufacturing process.

The disclosed embodiments show a hemispherical dome as the structure for performing the function of reflecting light toward the sample, but the structure for reflecting light toward the sample can be any other structure capable of performing the function of reflecting light toward the sample, including, by way of example an aspherical dome, a geodesic dome, a polyhedral section or at least one (a)spherical, polyhedral and/or other shape(s).

While not being limited to any particular performance indicator or diagnostic identifier, preferred embodiments of the present disclosure can be identified one at a time by testing for the presence of uniform illumination. The test for the presence of uniform illumination can be carried out without undue experimentation by the use of a simple and conventional light meter used to take readings at a plurality of locating based on spherical coordinates across a section of the dome reflector. Among the other ways in which to seek embodiments having the attribute of uniform illumination guidance toward the next preferred embodiment can be based on the presence of uniform reflection from a planar homogeneous test sample.

Definitions

A semiconductor wafer is a silicon disc that has many layers of materials deposited and patterned on to it. A typical wafer to be inspected by the vision system will have multitude of regions that are visible as a pattern caused primarily by the metallic traces running across the wafer. The metallic traces are brighter than the silicon and other materials on the wafer.

A monochromatic light is one that is constructed with a source such as an LED that emits a narrow spectrum of light. The term light is intended to mean frequencies greater than or equal to approximately 300 GHz, as well as the microwave spectrum. The phrase white light source is intended to mean a source of actinic radiation with a spectral width of from approximately 450 nm to approximately 700 nm. The phrase broad spectrum light source is intended to mean a non-monochromatic source of actinic radiation. The phrase object holder is intended to mean a wafer holder or sample space or stage such as an end-effector for a semiconductor wafer or a lighting panel cover upon which an object of interest can be placed.

The terms program and software and/or the phrases program elements, computer program and computer software are intended to mean a sequence of instructions designed for execution on a computer system (e.g., a program and/or computer program, may include a subroutine, a function, a procedure, an object method, an object implementation, an executable application, The described embodiments and examples are illustrative only and not intended to be limiting. Although embodiments of the present disclosure can be implemented separately, embodiments of the present disclosure may be integrated into the system(s) with which they are associated. All the embodiments of the present disclosure disclosed herein can be made and used without undue experimentation in light of the disclosure. Embodiments of the present disclosure are not limited by theoretical statements (if any) recited herein. The individual steps of embodiments of the present disclosure need not be performed in the disclosed manner, or combined in the disclosed sequences, but may be performed in any and all manner and/or combined in any and all sequences. The individual components of embodiments of the present disclosure need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials.

Various substitutions, modifications, additions and/or rearrangements of the features of embodiments of the present disclosure may be made without deviating from the scope of the underlying inventive concept. All the disclosed elements and features of each disclosed embodiment can be combined with, or substituted for, the disclosed elements and features of every other disclosed embodiment except where such elements or features are mutually exclusive. The scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" "mechanism for" and/or "step for". Subgeneric embodiments of the invention are delineated by the appended independent claims and their equivalents. Specific embodiments of the invention are differentiated by the appended dependent claims and their equivalents.

What is claimed is:

1. A method, comprising illuminating a reflective dome having a reflectance gradient with light from a light source, wherein the reflectance gradient is a function of position relative to a base plane defined by an edge of the reflective dome;
   illuminating an object substantially homogeneously with light reflected by the reflectance gradient of the reflective dome; and
   sensing light from the object through an aperture in the reflective dome,
   wherein sensing light from the object through an aperture includes sensing light from the object through a small aperture in the reflective dome.

2. The method of claim 1, wherein the reflective dome includes a shell of variable thickness that defines a gradient that increases toward the aperture to provide the reflective gradient whereby reflectivity increases toward the aperture.

\* \* \* \* \*